United States Patent
Dosi et al.

(10) Patent No.: US 9,394,245 B2
(45) Date of Patent: Jul. 19, 2016

(54) PROCESS FOR SULFONATING HALOBENZENE DERIVATIVES WITH SULFUR TRIOXIDE

(71) Applicant: SOLVAY SPECIALTY POLYMERS USA, LLC., Alpharetta, GA (US)

(72) Inventors: Mahendra Dosi, Alpharetta, GA (US); Ziad Husein, Evans, GA (US); Ronald Mysona, Evans, GA (US)

(73) Assignee: SOLVAY SPECIALTY POLYMERS USA, LLC., Alpharetta, GA (US)

( * ) Notice: Subject to any disclaimer, the term of this patent is extended or adjusted under 35 U.S.C. 154(b) by 0 days.

(21) Appl. No.: 14/422,445

(22) PCT Filed: Aug. 13, 2013

(86) PCT No.: PCT/EP2013/066909
§ 371 (c)(1),
(2) Date: Feb. 19, 2015

(87) PCT Pub. No.: WO2014/029666
PCT Pub. Date: Feb. 27, 2014

(65) Prior Publication Data
US 2015/0191425 A1 Jul. 9, 2015

Related U.S. Application Data

(60) Provisional application No. 61/684,885, filed on Aug. 20, 2012.

(30) Foreign Application Priority Data

Nov. 23, 2012 (EP) ..................................... 12194002

(51) Int. Cl.
C07C 303/06 (2006.01)
C01B 17/76 (2006.01)

(52) U.S. Cl.
CPC ............... *C07C 303/06* (2013.01); *C01B 17/76* (2013.01)

(58) Field of Classification Search
CPC ............................ C07C 303/06; C07C 309/39
See application file for complete search history.

(56) References Cited

U.S. PATENT DOCUMENTS

| 2,799,560 | A | * | 7/1957 | Davies | 423/535 |
| 2,835,708 | A | * | 5/1958 | Kamlet | 568/769 |
| 3,372,188 | A | | 3/1968 | Alston et al. | |
| 3,427,342 | A | | 2/1969 | Brooks et al. | |
| 5,264,200 | A | | 11/1993 | Felthouse et al. | |
| 5,911,958 | A | | 6/1999 | Dahl | |
| 6,521,200 | B1 | | 2/2003 | Silveston et al. | |
| 6,572,835 | B1 | | 6/2003 | MacArthur et al. | |
| 6,758,910 | B2 | | 7/2004 | Schmoyer | |
| 7,740,827 | B2 | | 6/2010 | Felthouse et al. | |
| 7,968,742 | B2 | | 6/2011 | Aigner et al. | |

FOREIGN PATENT DOCUMENTS

| GB | 2088350 A | 6/1982 |
| JP | H 09188663 A | 7/1997 |
| JP | 2001181255 A | 7/2001 |
| RO | 113981 B1 | 12/1998 |

OTHER PUBLICATIONS

Cerfontain et al. Canadian Journal of Chemistry (1994), 72(9), p. 1966-1971.*
Spryskov, A.A., et al—"Orientation in Substitution in the Aromatic Nucleus. IV. Sulfonation of Chlorobenzene", Jul. 1958, Journal of General Chemistry of the USSR, vol. 28, Issue No. 7, XP9168884A, pp. 2250-2254, English Translation; 7 pgs.
"Sulfur Trioxide", WIKIPEDIA, the free encyclopedia, Apr. 18, 2013, p. 1-4—retrieved from the Internet : URL:http://en.wikipedia.org/wiki/Sulfur_trioxide_on_2013-04-19; 4 pgs.
Gilbert, E. E., Et Al—"Sulfonation and Sulfation with Sulfur Trioxide", 1953, Journal of Industrial and Engineering Chemistry (Washington, D. C.) (1953), vol. 45, Issue No. 9, pp. 2065-2072; 8 pgs.
Sohrab,I M., "The Use of Double Mixed Reactors in Study and Modeling of Gas-liquid Reaction Rates", 1986, Preprints—American Chemical Society, Division of Petroleum Chemistry, 31, (3-4), pp. 649-54; 6 pgs.
Sohrabi, M., "The Use of Double Mixed Reactors in Study and Modelling of Gas-Liquid Reaction Rates", 1988, Afinidad XLV, 45, (418), pp. 547-550; 4 pgs.
Fine Organic Synthesis Technology/Chief editor: Lin Feng, Beijing: Science Press, 2006.
Study on Synthesis of Parachlorophenylsulfonic Acid by Sulfur Trioxide Method Nang Qinbao, Bao Yanfen, Yan Haicheng, Wang Qingquan, Liaoning Chemical Industry, vol. 27, No. 5, Sep. 1998.

* cited by examiner

*Primary Examiner* — Yong Chu
(74) *Attorney, Agent, or Firm* — Jarrod N. Raphael; Dwight M. Benner, II

(57) ABSTRACT

A process for sulfonating at least one halobenzene with sulfur trioxide ($SO_3$) comprising the following steps: Step 1. manufacturing a gaseous mixture [mixture (M)] comprising $SO_3$ and at least one additional gas different from $SO_3$ by oxidizing sulfur dioxide in the presence of at least one catalyst, wherein the $SO_3$ content in mixture (M) is from 1 to 95% by volume, relative to the total volume of mixture (M); and step 2 contacting said mixture (M) with said at least one halobenzene.

20 Claims, No Drawings

PROCESS FOR SULFONATING HALOBENZENE DERIVATIVES WITH SULFUR TRIOXIDE

This application claims priority to U.S. provisional application No. 61/684,885 filed on 20 Aug. 2012 and to European application No. 12194002.7 filed on 23 Nov. 2012, the whole content of each of these applications being incorporated herein by reference for all purposes.

TECHNICAL FIELD

The present invention relates to a process for sulfonating halobenzene with gaseous sulfur trioxide ($SO_3$) mixtures.

BACKGROUND ART

Sulfuric acid ($H_2SO_4$) and oleum (which is a solution of sulfur trioxide in concentrated sulfuric acid namely $SO_3 \cdot H_2SO_4$) are widely used as sulfonating agents for the sulfonation of aromatic compounds. Sulfuric acid ($H_2SO_4$) and oleum always need to be used in large excess as water is formed in the sulfonating reaction thereby diluting the oleum and/or sulfuric acid. This has the disadvantage of leaving large quantities of unreacted sulfuric acid. This waste acid must be separated from the reaction mixture and subsequently disposed of. This acid is difficult to dispose of, either as the free acid or in the form of soluble or insoluble sulfates, particularly now when effluent requirements are becoming more stringent.

Alternatively, sulfur trioxide itself in gaseous or liquid form, has also been used for the sulfonation of aromatic compounds. Sulfur trioxide reacts instantaneously with aromatic compounds, and it is not necessary to use a substantial excess to realize complete sulfonation. There is, therefore, no need for the reaction product to be contaminated with substantial quantities of excess sulfonating agent. Sulfur trioxide itself can notably be prepared from oleum. For example, distillation of oleum can generate pure $SO_3$ vapour which can be used as such or can be further condensed to form pure liquid $SO_3$. However, pure gaseous or liquid sulfur trioxide is very highly reactive and its reactions with aromatic compounds are extremely exothermic and difficult to control and undesirable side reactions might occur. It is known that in order to moderate and control the reactions of pure gaseous or liquid $SO_3$ with aromatic compounds, $SO_3$ has been used in the presence of inert diluents. For example, air/$SO_3$ sulfonation processes are widely used in the surfactants and detergent industry for the sulfonation of long chain and/or high molecular weight organics, such as for example low volatile long chain alkyl benzenes, which are characterized by having high viscosity and high flash points.

The diluted, gaseous $SO_3$ mixture is still a very aggressive/reactive material.

For this reason, it is known that the use of the air/$SO_3$ sulfonation process for the sulfonation of more volatile compounds such as notably toluene, xylene and other lower alkyl benzenes are problematic and said process is in general less suitable for the sulfonation of volatile aromatic compounds.

Thus, there is still a considerable need for a process for sulfonating volatile halobenzene compounds with sulfur trioxide ($SO_3$) in a controllable manner, which avoids the use of liquid $SO_3$ which entails some serious concern for its security, transportation, and rigorous storage requirements imposed by the hazardous nature of liquid $SO_3$, capable of providing para-substituted halobenzene sulfonic acid compounds in high yield and 4,4'-dihalodiphenyl sulfone, both in high purity and high selectivity, to minimize of any formation of oversulfonated products as a result of undesirable side reactions and avoid unconverted reactants, yet without any significant problem of disposal of excess sulphuric acid, much less hazardous for the environment and simultaneously in achieving significant cost savings.

SUMMARY OF INVENTION

The present invention thus relates to a process for sulfonating at least one halobenzene with sulfur trioxide ($SO_3$) comprising the following steps:

Step 1. manufacturing a gaseous mixture [mixture (M)] comprising $SO_3$ and at least one additional gas different from $SO_3$ by oxidizing sulfur dioxide ($SO_2$) in the presence of at least one catalyst, wherein the $SO_3$ content in mixture (M) is from 1 to 95% by volume, relative to the total volume of mixture (M); and Step 2. contacting said mixture (M) with said at least one halobenzene.

For the purpose of the present invention, the term "halobenzene" is intended to denote any halogenated derivative of benzene. It may be mono-, di- or tri-halogenated. The halobenzene is preferably a monohalobenzene where the halogen atom is chosen from chloride, fluoride, bromide and iodide. More preferably, the halobenzene is monochlorobenzene (MCB).

DETAILED DESCRIPTION OF EMBODIMENTS

Mixture (M)

As said, the mixture (M) prepared in the first step of the process of the present invention comprises $SO_3$ and at least one additional gas different from $SO_3$.

For the purpose of the present invention, the additional gas different from $SO_3$ is an inert gas.

For the purpose of the present invention, the term "inert gas" denotes a gas which is substantially unreactive during the course of the sulfonation reaction.

The additional gas different from $SO_3$ is preferably selected from a group consisting of air, nitrogen, carbon dioxide, oxygen, sulfur dioxide ($SO_2$), in particular unconverted $SO_2$ and mixtures thereof. More preferably, the additional gas different from $SO_3$ is nitrogen, air or a mixture of nitrogen and air or a mixture of air and unconverted $SO_2$. Most preferably, the additional gas different from $SO_3$ is a mixture from air and unconverted $SO_2$.

The expression 'air' is to be understood according to its usual meaning, i.e. atmospheric air at sea level, which typically includes about 78.1% by volume nitrogen gas ($N_2$), about 20.9% by volume oxygen gas ($O_2$) and less that 1% by volume of Argon (Ar) relative to the total volume of air.

In the process according to the invention and in the particular embodiments thereof, the $SO_3$ content in mixture (M) is advantageously from 1 to 95% by volume, preferably from 1 to 70% by volume, more preferably from 2 to 50% by volume, even more preferably from 3 to 20% by volume, most preferably from 4 to 8% by volume relative to the total volume of mixture (M).

If desired, the mixture (M) consists of $SO_3$ and the additional gas different from $SO_3$.

In a particular preferred embodiment of the present invention, the mixture (M) is a $SO_3$/unconverted $SO_2$/air mixture in which the $SO_3$ content is advantageously from 1 to 95% by volume, preferably from 1 to 70% by volume, more preferably from 2 to 50% by volume, even more preferably from 3 to 20% by volume, most preferably from 4 to 8% by volume relative to the total volume of the $SO_3$/unconverted $SO_2$/air mixture.

For the purpose of the present invention, the term "unconverted $SO_2$" refers to the $SO_2$ that has not been oxidized.

In one embodiment of the present invention, the unconverted $SO_2$ content in the $SO_3$/unconverted $SO_2$/air mixture is in general equal to or below 10% by mole, preferably equal to or below 5% by mole, more preferably equal to or below 4% by mole, most preferably equal to or below 2% by mole, based on the total moles of $SO_3$ and unconverted $SO_2$.

Good results were obtained with a 2% by mole to 4% by mole of unconverted $SO_2$ content in the $SO_3$/unconverted $SO_2$/air mixture, based on the total moles of $SO_3$ and unconverted $SO_2$.

In Step 1. of the present invention, the manufacturing of mixture (M) is performed by oxidizing sulfur dioxide ($SO_2$) in the presence of at least one catalyst.

For the purpose of the present invention, any catalyst known in the art that can be used to oxidize $SO_2$ to $SO_3$ is suitable.

Typical examples of suitable catalysts that may be used in the present invention include, but are not limited to, solid particulate catalysts typically containing an alkali-vanadium or platinum-containing active phase such as notably described in U.S. Pat. No. 5,264,200, the whole content of which is herein incorporated by reference, commercially available vanadium pentoxide ($V_2O_5$), ruthenium oxide such as notably described in U.S. Pat. No. 7,740,827, the whole content of which is herein incorporated by reference. Good results were obtained with commercially available vanadium pentoxide ($V_2O_5$).

If desired, the oxidation of $SO_2$ to $SO_3$ can be carried out in a multiple stage catalytic converter such as notably described in U.S. Pat. No. 7,740,827 and references therein. A specific example of a multiple stage catalytic converter is notably a three-stage vanadium pentoxide catalytic converter.

In Step 1. of the process of the invention, the oxidation of $SO_2$ to $SO_3$ in the presence of at least one catalyst is typically carried out in the presence of air, oxygen enriched air or neat oxygen or oxygen-containing gases. Preferred, said oxidation is carried out in the presence of air.

In one specific embodiment of Step 1. of the present invention, gaseous $SO_2$ is mixed with preheated air to form a gaseous sulfur dioxide/air mixture [mixture ($M_{SO2/air}$)].

In this specific embodiment, the preheated air has advantageously a temperature equal to or less than 600° C., more preferably equal to or less than 480° C.

The preheated air has advantageously a temperature equal to or above 350° C., more preferably equal to or above 400° C.

Preheated air having a temperature of 450° C. gave particularly good results.

The preheated air, mentioned above, is preferably dry and the removal of water in the preheated air may be accomplished by any conventional means such as notably vapor tubes and the like. The water content in the preheated air is advantageously equal to or less than about 0.01% by volume, preferably equal to or less than 0.001% by volume, based on the total volume of the mixture ($M_{SO2/air}$).

It is known in the art that a specific temperature range from 416 to 454° C. is favorable to initiate the catalytic conversion of $SO_2$ to $SO_3$. If desired, the temperature can be changed after the conversion reaction is initiated.

The conversion of $SO_2$ to $SO_3$ is an equilibrium reaction ($SO_2+[\frac{1}{2}]O_2 \leftrightarrows SO_3$). The oxygen required to convert $SO_2$ to $SO_3$ is typically provided by the air in the mixture ($M_{SO2/air}$). The percentage of $SO_2$ which can be converted to $SO_3$ varies with temperature and with the concentration (partial pressure) of the gaseous initial reactants, namely $SO_2$ and $O_2$. The person skilled in the art will use standard techniques and routine work so as to determine temperature and concentration of the gaseous initial reactants for obtaining the final desired conversion of $SO_2$ to $SO_3$. The conversion of $SO_2$ to $SO_3$ is typically in the range from 96% to 98%, preferably exceeds 96%.

It is known that the lower the temperature in the standard temperature range at which the conversion reaction occurs, the greater the conversion of $SO_2$ to $SO_3$. For a given concentration of reactants and assuming the conversion reaction proceeds to equilibrium, there is a theoretical conversion percentage of $SO_2$ to $SO_3$ at each temperature within the range at which conversion can be sustained. The conversion temperature range has maximum and minimum temperatures. Maximum theoretical conversion occurs at the minimum temperature at which conversion can be sustained. Depending upon the concentration of the reactants, maximum theoretical conversion can be 99 percent or more, at a minimum sustaining temperature of for example 400° C.

As noted above, there is a maximum temperature at which the conversion reaction can be sustained, and the maximum sustaining temperature decreases as the conversion percentage increases. For example, depending upon the concentration of the initial reactants, at a temperature of about 600° C. the conversion reaction reaches equilibrium when the theoretical $SO_3$ percentage is about 70 percent; a lower temperature, e.g., about 480° C. or below, may be required to obtain a theoretical conversion of 95 percent, and a temperature of about 400° C. may be required to obtain a theoretical conversion of 99 percent.

In this specific embodiment of Step 1. according to the present invention, the $SO_2$ content in the mixture ($M_{SO2/air}$) is from 0.1 to 30% by volume, more preferable from 0.5 to 15% by volume, most preferably from 1 to 5% by volume relative to the total volume of the mixture ($M_{SO2/air}$).

In this specific embodiment of Step 1. according to the present invention, the $O_2$ content in the mixture ($M_{SO2/air}$) is from 15 to 25% by volume, most preferably from 19 to 21% by volume relative to the total volume of the mixture ($M_{SO2/air}$).

Gaseous $SO_2$ is generally obtained by evaporation of liquid $SO_2$ which is for example commercially available in large containers as well as in small lab cylinders. The evaporated $SO_2$ can then be mixed with preheated air to form the mixture ($M_{SO2/air}$), as described above.

In an alternative embodiment, a gaseous sulfur dioxide/air mixture can be produced by reacting sulfur and air in a sulfur burner such as notably described in U.S. Pat. No. 6,572,835 B1 the whole content of which is herein incorporated by reference and UK published patent application GB 2 088 350 A, the whole content of which is herein incorporated by reference.

The Applicant has surprisingly found that the mixture (M) as mentioned above, is effective in sulfonating at least one halobenzene by contacting said at least one halobenzene.

In a preferred embodiment of the present invention, the mixture (M) is contacted with at least one halobenzene without any preliminary separation/purification step of said mixture (M).

If desired, the mixture (M) can be further purified by notably removing the unconverted $SO_2$, or can be further enriched or diluted with the at least one additional gas different from $SO_3$, as described above, before said mixture (M) is contacted with at least one halobenzene.

If desired, said mixture (M) can be stored.

In a particular preferred embodiment of the present invention, the process for sulfonating at least one halobenzene with sulfur trioxide ($SO_3$) comprising the Steps 1. and Steps 2. are carried out with no intermediate separation or storage of the mixture (M).

Step 2. according to the present invention is advantageously carried out by contacting the mixture (M) with the at least one halobenzene in a suitable reactor.

The choice of the reactor is not critical, provided that the reactor can enable an efficient contact between the mixture (M) and at least one halobenzene, a removal of the exothermic heat of reaction, and is foreseen with means for escape of effluent vapor streams and avoid $SO_3$ loss in said effluent vapor streams.

Among suitable reactors, mention can be made of, but not limiting to film reactors, including notably the Falling Film Reactor as described for example in U.S. Pat. Nos. 7,968,742 B2 and 5,911,958, the whole content of which is herein incorporated by reference, dispersed phase or jet reactors, stirred tank reactors, continuous stirred tanks (CSTR) and cascades of at least two or 3 continuous stirred tanks which can optionally be equipped with a means to enable a counter-current flow of the halobenzene and the mixture (M). Preferred will be the Falling Film Reactors, stirred tank reactors and cascades of at least two or 3 continuous stirred tanks optionally equipped with a means to enable a counter-current flow of the halobenzene and the mixture (M).

In general, the reactor is also additionally equipped with at least one nozzle-set; stirring means; means for feeding the reactants including notably gas flow means, dosing/metering systems such as for example a rotameter for converter gas dosing or a semi-automatic burette for liquids, and the like; temperature control means, such as for example a thermocouple and heat exchangers so as to obtain carefully controlled conditions of $SO_3$/halobenzene molar ratio, temperature and $SO_3$ concentration.

Any nozzle-set suitable for mixing of the halobenzene and the mixture (M) can be used.

Among suitable nozzle-sets, mention can be made of, but not limiting to a ring fitted with multi-nozzles, 12-nozzle disperser, or a flow pipe with a sparger. Non limiting examples of stirring means in the reaction medium may be notably means of internal stirring such as a turbine or an agitator, or by means of a recirculation pipe exterior to the reactor. Optimal stirring can advantageously ensure good mixing, in particular good dispersion, of the mixture (M) into halobenzene.

Any heat-exchanger suitable for reconverting by cooling the volatized reaction medium to liquid, in particular the halobenzene, so that said liquid can be returned to the reaction mixture can be used. A typical heat-exchanger is notably a water-cooled condenser. It has been found that the heat-exchanger advantageously avoid the loss of the halobenzene in the effluent vapor stream.

In Step 2. of the process according the present invention, the $SO_3$/halobenzene molar ratio is advantageously from 0.17 to 3, preferably from 0.25 to 1.2, more preferably from 0.5 to 1.0.

In Step 2. of the process according the present invention, the $SO_3$/halobenzene molar ratio is advantageously above 0.17, preferably above 0.25.

For the purpose of the present invention, the $SO_3$/halobenzene molar ratio is defined as the ratio between the total number of moles of $SO_3$, present in the mixture (M), as described above, fed to the reactor divided by the total number of moles of halobenzene fed to the same reactor.

In a specific preferred embodiment of the present invention, in Step 2. of the process, the $SO_3$/MCB molar ratio is advantageously from 0.17 to 3, preferably from 0.25 to 1.2, more preferably from 0.5 to 1.0.

In this specific preferred embodiment, the $SO_3$/MCB molar ratio is advantageously above 0.17, preferably above 0.25.

The $SO_3$/halobenzene molar ratio can be varied or kept constant during the reaction time depending on the feed of the mixture (M) and the feed of the halobenzene, in particular MCB, to the reactor.

In Step 2. of the process according the present invention, the feeding of halobenzene, in particular MCB to the reactor can be realized by a one single batch addition at the start of the reaction, by sequentially multiple batch additions or a continuous feed of halobenzene.

In one embodiment of Step 2. of the present invention, the halobenzene is charged into the reactor in one single batch at the start of the reaction.

In another embodiment of Step 2. of the present invention, the halobenzene is sequentially fed to the reactor in multiple batch additions.

In another embodiment of Step 2. of the present invention, the halobenzene is fed to the reactor by a continuous feed of the halobenzene. In this embodiment, it is beneficial, to keep the $SO_3$/halobenzene molar ratio constant by controlling the feed flow rate of the halobenzene, in particular MCB, during the reaction time. Generally the feed flow rate of the halobenzene, in particular MCB is adapted to the feed flow rate of the mixture (M) in order to comply with the desired $SO_3$/halobenzene molar ratio, as mentioned above.

Generally the flow rate of said feeding is equal to or less than 22000 l per hour (l/h), preferably equal to or less than 15000 l/h, more preferably equal to or less than 2000 l/h, even more preferably equal to or less than 240 l/h.

Generally, the flow rate of the feeding of the halobenzene is equal to or more than 0.1 l/h, preferably equal to or more than 10 l/h, more preferably equal to or more than 140 l/h.

In Step 2. according to the invention and in the particular embodiments thereof, it is especially beneficial to control the feeding of the mixture (M) to the reactor so as to avoid notably that halobenzene is not volatilized by the heat of the reaction more rapidly than the heat-exchanger is able to reconvert it to the liquid state. Generally the flow rate of said feeding is equal to or less than 1500 liter per hour (l/h), preferably equal to or less than 500 liter per hour (l/h), more preferably equal to or less than 380 liter per hour (l/h).

Generally, the flow rate of the feeding of the mixture (M) is equal to or more than 10 liter per hour (l/h), preferably equal to or more than 300 liter per hour (l/h), more preferably equal to or more than 320 liter per hour (l/h).

Flow rates of the feeding of the mixture (M) In Step 2. of the process according the present invention from 320 l/h to 380 l/h gave particularly good results, a flow rate of 350 l/h gave excellent result.

The flow rates of the feeding of the mixture (M) are typically controlled by gas flow means known to the person skilled in the art such as for example a gas rotameter, mass flow meter and the like.

Step 2. of the process according the present invention is preferably carried out at a temperature of below 200° C., more preferably of below 160° C., still more preferably of below 130° C. and most preferably of below 100° C.

Step 2. of the process according the present invention is preferably carried out at a temperature of above −40° C., more preferably of above 0° C., still more preferably of above 20° C. and most preferably of above 40° C.

Step 2. of the process according the present invention is preferably carried out at a pressure of below 10 atm, more preferably of below 7 atm, still more preferably of below 5 atm and most preferably of below 2 atm.

Step 2. of the process according the present invention is preferably carried out at a temperature of above 0.5 atm, more preferably of above 0.6 atm, still more preferably of above 0.7 atm and most preferably of above 0.8 atm.

Excellent results were obtained when Step 2. of the process according the present invention was carried out at atmospheric pressure.

It has been found that the process according to the invention allows a decreased loss of $SO_3$ in the effluent vapor streams.

It is understood that the different processes and embodiments disclosed herein apply in a most preferred way to the sulfonation of monochlorobenzene (MCB) with sulfur trioxide ($SO_3$) yielding a sulfonated product mixture comprising mainly the desired para-chlorobenzene sulfonic acid (para-CBSA) and the desired 4,4'-dichlorodiphenyl sulfone together with minor amounts of ortho-chlorobenzene sulfonic acid (ortho-CBSA), meta-chlorobenzene sulfonic acid (meta-CBSA), 2,4'-dichlorodiphenyl sulfone, 3,4'-dichlorodiphenyl sulfone, 2 sulfone sulfonic acid isomers, sulfuric acid and unreacted halobenzene. It has been suggested that in the sulfone sulfonic acid isomers, an additional sulfonating of one of the two benzene rings in the sulfone has taken place.

Should the disclosure of any patents, patent applications, and publications which are incorporated herein by reference conflict with the description of the present application to the extent that it may render a term unclear, the present description shall take precedence.

EXAMPLES

The invention will now be described in more details with reference to the following examples, whose purpose is merely illustrative and not intended to limit the scope of the invention.

General Procedure for the Sulfonation of Monochlorobenzene (MCB)

Liquid $SO_2$ supplied in commercial lab cylinders was heated and vaporized, said vaporized $SO_2$ was flowed into to the three-stage vanadium pentoxide ($V_2O_5$) catalytic converter along with an air stream preheated at 450° C. The flow rates of $SO_2$ and air in the feed were adjusted to yield a desired $SO_3$ content of 8% by volume relative to the total volume of air/$SO_3$ product stream. The $SO_2$ was converted to $SO_3$ up to 96-98% thereby providing an air/$SO_3$/$SO_2$(unconverted) mixture which is subsequently used without further purification. Said air/$SO_3$/$SO_2$(unconverted) mixture obtained was continuously fed with a flow rate of 350 liter/hr (controlled by a rotameter) into a jacketed cylindrical glass flask, which was one-liter in size, fitted with a stirrer, a condenser and a thermocouple. Said air/$SO_3$/$SO_2$(unconverted) mixture was dispersed into the liquid content of the reactor through a 12-nozzle disperser. The reactor temperature, as indicated in Table 1 was controlled by circulating water in the reactor jacket from a water bath. Liquid monochlorobenzene (MCB) was initially charged into the glass flask and/or added in batch to the flask and/or continuously fed into the reactor using a semi-automatic burette with a specific flow rate as specified below. The loss of $SO_3$, present in the non-condensable gas leaving the condenser was scrubbed with water in three stages. The loss of $SO_3$ in reactor effluent vapor was determined using acid analysis of the scrubbed water samples. During the reaction and at the end of the reaction, the reaction mixture and the final reaction product mixture, respectively were analysed by GC, LC, GC/MS (gas chromatography coupled to mass spectrometry) and LC/MS (liquid chromatography coupled to mass spectrometry). The experimental data are summarized in Tables 1 and 2.

Example 1

The general procedure, as detailed above, was followed whereby liquid monochlorobenzene (MCB) was initially charged into the glass flask in an amount of 250 ml and with no additions of MCB. The sulfonation was carried out at a temperature of 30° C.

Example 2

The general procedure, as detailed above, was followed whereby liquid monochlorobenzene (MCB) was initially charged into the glass flask in an amount of 250 ml and after every 30 minute, 20 ml of MCB was added in batch. Initially the reaction temperature was maintained at 30° C. The temperature was increased to 45° C., 60° C. and 75° C. at 60, 90 and 120 minutes, respectively. The reaction at 75° C. was extended for another 30 minutes with no further addition of MCB.

Comparative Example 3 (Cex 3)

Liquid monochlorobenzene (MCB) and liquid $SO_3$ were charged continuously to a larger production-scale continuous reactor. The liquid $SO_3$ and liquid MCB were fed with a flow rate of 500 Kg/hr (260 liter/hr) and 1500 Kg/hr (1350 liter/hr), respectively. The mole ratio liquid $SO_3$/liquid MCB was 0.47. The MCB entered the reactor through the reactor vent scrubber which eliminated any loss of $SO_3$ vapour into the vent. The reactor temperature was maintained constant at 70° C. Since the sulfonation reaction is exothermic, reactor liquid was cooled by recirculation through an external heat exchanger. After steady state reaction conditions were attained, the reactor products were removed continuously keeping the liquid level constant in the reactor.

TABLE 1

| | Example 1 | | | Example 2 | | | | Cex 3 |
|---|---|---|---|---|---|---|---|---|
| Test Conditions | | | | | | | | |
| $SO_3$ content (%) by volume relative to the total volume of air/$SO_3$ stream | 8 | 8 | 8 | 8 | 8 | 8 | 8 | — |

TABLE 1-continued

|  | Example 1 | | Example 2 | | | | | Cex 3 |
|---|---|---|---|---|---|---|---|---|
| Reaction time (min) | 120 | 135 | 30 | 60 | 90 | 120 | 150 | Continous feed |
| Reaction temperature (° C.) | 30 | 30 | 30 | 45 | 60 | 75 | 75 | 70 |
| Reaction products | | | | | | | | |
| chlorobenzene sulfonic acid (CBSA) wt. % | 86 | 83 | 29 | 47 | 65 | 77 | 74 | 44.5 |
| Isomers of CBSA | | | | | | | | |
| para-CBSA (% mole) | 98.1 | 98.1 | 99.0 | 98.8 | 98.6 | 98.0 | 97.8 | 95.1 |
| ortho-CBSA (% mole) | 1.6 | 1.6 | 0.8 | 0.9 | 1.1 | 1.6 | 1.7 | 3.5 |
| meta-CBSA (% mole) | 0.4 | 0.4 | 0.2 | 0.3 | 0.3 | 0.4 | 0.5 | 1.4 |
| dichlorodiphenyl sulfone wt. % | 8 | 9 | <1 | <1 | 3 | 7 | 10 | 7.4 |
| Isomers of sulfone | | | | | | | | |
| 4,4'-isomer (% mole) | 95.6 | 95.6 | | | 95.6 | 95.4 | 95.3 | 93.3 |
| 2,4'-isomer (% mole) | 3.9 | 4.0 | | | 3.9 | 3.8 | 4.0 | 4.9 |
| 3,4'-isomer (% mole) | 0.5 | 0.4 | | | 0.5 | 0.8 | 0.7 | 1.8 |
| Isomers of sulfone sulfonic acid | | | | | | | | |
| Isomer 1 wt. % | — | — | | | — | — | 1.0 | — |
| Isomer 2 wt. % | — | — | | | — | — | <1 | — |
| $H_2SO_4$ wt. % | 6 | 8 | 1 | 2 | 2 | 6 | 14 | 3.3 |
| Unreacted and Loss products | | | | | | | | |
| MCB wt. % | — | — | 69 | 51 | 30 | 10 | — | 44.8 |
| % of supplied $SO_3$ lost in non-condensable gas | — | — | 1.1 | 6.6 | 5.7 | 4.6 | 2.6 | — |

It has been found that the overall chemical reactions taking place in Examples 1 and 2, carried out according to he present invention by using an air/$SO_3$/$SO_2$ (unconverted) mixture yielded no new products when compared with the products obtained by sulfonation of MCB using liquid $SO_3$ (Cex 3) and the desired para-chlorobenzene sulfonic acid and 4,4'-dichlorodiphenyl sulfone could be obtained in higher yield.

The invention claimed is:

1. A process for sulfonating at least one monohalobenzene with sulfur trioxide ($SO_3$) comprising the following steps—:
   Step 1. manufacturing a gaseous mixture (M) comprising $SO_3$ and at least one additional gas different from $SO_3$, by oxidizing sulfur dioxide ($SO_2$) in the presence of at least one catalyst, wherein the $SO_3$ content in the mixture (M) is from 1 to 95% by volume, relative to a total volume of the mixture (M)—; and
   Step 2. contacting the mixture (M) with the at least one monohalobenzene.

2. The process according to claim 1, wherein in Step 1. the additional gas different from $SO_3$ is selected from a group consisting of air, nitrogen, carbon dioxide, oxygen, sulfur dioxide ($SO_2$), and mixtures thereof.

3. The process according to claim 1, wherein in Step 1. the mixture (M) comprises $SO_3$, unconverted $SO_2$, and air in which the $SO_3$ content is from 1 to 95% by volume, relative to a total volume of the $SO_3$/air mixture.

4. The process according to claim 1, wherein in Step 1. the oxidation of $SO_2$ to $SO_3$ in the presence of the at least one catalyst is carried out in the presence of air, oxygen enriched air, neat oxygen, or oxygen-containing gases.

5. The process according to claim 4, wherein the $SO_2$ is mixed with preheated air to form a gaseous sulfur dioxide/air mixture ($M_{SO2/air}$).

6. The process according to claim 5, wherein in Step 1. the sulfur dioxide/air mixture ($M_{SO2/air}$) comprises from 0.1 to 30% of $SO_2$ by volume relative to a total volume of the mixture ($M_{SO2/air}$).

7. The process according to claim 5, wherein the sulfur dioxide/air mixture ($M_{SO2/air}$) comprises from 15 to 25% of $O_2$ by volume relative to a total volume of the mixture ($M_{SO2/air}$).

8. The process according to claim 1, wherein in Step 2. the mixture (M) is contacted with the at least one monohalobenzene without any preliminary separation or purification step of the mixture (M).

9. The process according to claim 1 further comprising a molar ratio of $SO_3$/monohalobenzene from 0.17 to 3 in Step 2.

10. The process according to claim 1 further comprising in Step 2. feeding the at least one monohalobenzene into a reactor by one single batch addition at the start of the reaction, by sequential multiple batch additions, or by continuously feeding the at least one monohalobenzene into the reactor.

11. The process according to claim 10, wherein the at least one monohalobenzene is continuously fed into the reactor at a flow feeding rate equal to or less than 22000 liter per hour (l/h).

12. The process according to claim 10 further comprising in Step 2. feeding the mixture (M) into the reactor at a flow feed rate equal to or less than 1500 liter per hour (l/h).

13. The process according to claim 1, wherein step 2 is carried out at a temperature of below 200° C.

14. The process according to claim 1, wherein step 2 is carried out at a pressure of below 10 atm.

15. The process according to claim 1, wherein the at least one monohalobenzene is monochlorobenzene (MCB).

16. The process according to claim 2, wherein the sulfur dioxide ($SO_2$) is unconverted $SO_2$.

17. The process according to claim 1, wherein the process produces at least para-substituted halobenzene sulfonic acid compounds, 4,4'-dihalodiphenyl sulfones, and mixtures thereof.

18. The process according to claim 1, wherein the process produces at least para-chlorobenzene sulfonic acid, 4,4'dichlorodiphenyl sulfone, and mixtures thereof.

19. The process according to claim 16, wherein 96% to 98% of the $SO_2$ is converted to the $SO_3$ by oxidation.

20. The process according to claim 1, wherein more than 96% of the $SO_2$ is converted to the $SO_3$ by oxidation.

* * * * *